United States Patent
Hayashi et al.

(10) Patent No.: US 10,386,236 B2
(45) Date of Patent: Aug. 20, 2019

(54) REFLECTED LIGHT DETECTING DEVICE AND REFLECTED LIGHT DETECTING METHOD

(71) Applicant: NATIONAL UNIVERSITY CORPORATION KAGAWA UNIVERSITY, Takamatsu-shi, Kagawa (JP)

(72) Inventors: Hiroki Hayashi, Takamatsu (JP); Ichiro Ishimaru, Takamatsu (JP)

(73) Assignee: NATIONAL UNIVERSITY CORPORATION KAGAWA UNIVERSITY, Takamatsu-shi (JP)

(*) Notice: Subject to any disclaimer, the term of this patent is extended or adjusted under 35 U.S.C. 154(b) by 0 days.

(21) Appl. No.: 15/597,544

(22) Filed: May 17, 2017

(65) Prior Publication Data

US 2017/0336263 A1  Nov. 23, 2017

(30) Foreign Application Priority Data

May 20, 2016 (JP) .................. 2016-101747

(51) Int. Cl.
*G01B 9/02* (2006.01)
*G01J 3/447* (2006.01)
(Continued)

(52) U.S. Cl.
CPC .......... *G01J 3/447* (2013.01); *G01J 3/0224* (2013.01); *G01J 3/0289* (2013.01); *G01J 3/45* (2013.01);
(Continued)

(58) Field of Classification Search
CPC .. G01J 3/447; G01J 3/0224; G01J 3/45; G01J 3/2823; G01J 4/04; G01B 2290/70; G01B 9/02021; G01B 9/02097
(Continued)

(56) References Cited

U.S. PATENT DOCUMENTS

2002/0196438 A1* 12/2002 Kerschbaumer .......... G01J 3/50
356/327
2006/0279743 A1* 12/2006 Boesser ............... G01B 9/0207
356/500

FOREIGN PATENT DOCUMENTS

JP   2002-200050 A   7/2002
JP   2011-516112 A   5/2011
(Continued)

OTHER PUBLICATIONS

Oct. 2, 2018 Office Action issued in Japanese Patent Application No. 2016-101747.

*Primary Examiner* — Kara E. Geisel
*Assistant Examiner* — Jonathon Cook
(74) *Attorney, Agent, or Firm* — Oliff PLC

(57) ABSTRACT

Reflected light detecting device and method with surface reflected light components collectively be extracted/removed when detecting reflected light arising in casting light onto target-object range having non-planar surface. The device includes: a first illuminating device causing first-measurement light in predetermined polarization direction to enter target-object first region from first direction; polarization optical system position part of first-surface reflected light enters the polarization optical system, the first-surface reflected light being the first-measurement in the first region surface; a second illuminating device causing second-measurement light in the same first-measurement light polarization direction to enter second region from second direction, the second region being on the target-object surface, different from the first region; adjusting direction of the second-measurement light optical axis so part of second-surface reflected light enters the polarization optical system, the second-surface reflected light being the second-measure- (Continued)

ment in second region surface; and detecting light having passed through the polarization optical system.

6 Claims, 6 Drawing Sheets

(51) Int. Cl.
    *G01J 3/02*     (2006.01)
    *G01J 3/45*     (2006.01)
    *G01J 3/50*     (2006.01)
    *G01N 21/21*     (2006.01)
    *G01N 21/25*     (2006.01)
    *G01N 21/55*     (2014.01)

(52) U.S. Cl.
    CPC ............... *G01J 3/50* (2013.01); *G01N 21/21* (2013.01); *G01N 21/255* (2013.01); *G01N 21/55* (2013.01); *G01N 2021/217* (2013.01); *G01N 2021/559* (2013.01); *G01N 2201/0642* (2013.01)

(58) Field of Classification Search
    USPC ..... 356/453, 491, 239.7–239.8, 237.2–237.5
    See application file for complete search history.

(56) References Cited

FOREIGN PATENT DOCUMENTS

| | | |
|---|---|---|
| JP | 2014-023609 A | 2/2014 |
| WO | 2009/115947 A1 | 9/2009 |
| WO | 2014/054708 A1 | 4/2014 |

\* cited by examiner

VISUAL IMAGE

CCD IMAGE

CROSSED NICOL

PARALLEL NICOL

REFLECTED LIGHT DETECTING DEVICE AND REFLECTED LIGHT DETECTING METHOD

TECHNICAL FIELD

The present invention relates to a reflected light detecting device and a reflected light detecting method used for analyzing a target object using reflected light (surface reflected light and internally reflected light) arising from the target object when causing rays of light to enter the target object from a plurality of different directions.

BACKGROUND ART

It has been a conventional practice to perform qualitative and quantitative measurements of the surface shape and the color of an object, components contained in the object, and the like using reflected light resulting from casting light onto a predetermined measurement region on the surface of the object. The reflected light contains light reflected from a surface of the object (surface reflected light component) and light that enters the object and is reflected there (internally reflected light component). Either of the surface reflected light component and the internally reflected light component, or both of the surface reflected light component and the internally reflected light component are used depending on the target to be measured. When only one of the surface reflected light component and the internally reflected light component is used to measure the surface shape and the color of the object and components contained in the object, and the like, the other light component becomes noise. Hence, in order to enhance accuracy and sensitivity of the measurement, the other light component needs to be removed from the reflected light.

For example, Patent Literature 1 discloses a method of measuring the amounts of pigment such as melanin and hemoglobin forming the color of a skin using an internally reflected light component out of reflected light arising when light is cast from a light source onto a human face. When linearly polarized light is cast onto the surface of an object, surface reflection maintains the polarization state (oscillation direction) of the incident light, while internal reflections give non-polarized light since their reflecting directions and the oscillation directions are diverse. Therefore, in Patent Literature 1, a first polarizing filter is placed between the light source and the human face, and a second polarizing filter whose polarization direction is orthogonal to that of the first polarizing filter is placed between the human face and a light receiver, so that the surface reflected light component is removed from the reflected light.

CITATION LIST

Patent Literature

[Patent Literature 1] JP 2002-200050 A

SUMMARY OF INVENTION

Technical Problem

Since in Patent Literature 1, light is cast onto a relatively narrow region of the face, the reflected rays of light on the surface of the face have substantially the same direction. Accordingly, by setting the polarization direction of the first polarizing filter and the polarization direction of the second polarizing filter in the aforementioned relation, almost the entire surface reflected light can be removed. When the amounts and the distributions of pigment contained in the whole face by this method is to be measured, however, it is necessary to measure the reflected light while moving the casting region of light across whole of the face, which is time-consuming.

In such a case, rays of light may be cast onto the whole human face or a plurality of spots on the human face to collectively measure the resulting rays of reflected light. Casting rays of light onto an object having a non-planar surface, such as a face, however, causes various incident angles of the respective rays of light, and thus, results in various reflecting directions of surface reflected light. Moreover, different directions of surface reflection also lead to different oscillation directions. Accordingly, this method has a problem of insufficient removal of the rays of surface reflected light when only a single second polarizing filter is placed between the face and the light receiver.

While removal of surface reflected light is herein described, the same applies to extraction of surface reflected light.

A problem to be solved by the present invention is to provide a reflected light detecting device and a reflected light detecting method with which surface reflected light components can be collectively extracted or removed when detecting reflected light arising in casting light onto a wide range of a target object having a non-planar surface.

Solution to Problem

A reflected light detecting device according to the present invention devised in order to solve the aforementioned problem includes:

a) a first illuminating device for causing first measurement light in a predetermined polarization direction to enter a first region of a target object having a globally non-planar surface from a first direction;

b) a polarization optical system arranged at a position where at least part of first surface reflected light enters the polarization optical system, the first surface reflected light being the first measurement light reflected on a surface in the first region;

c) a second illuminating device for causing second measurement light in the same polarization direction as that of the first measurement light to enter a second region from a second direction, the second region being located on the surface of the target object and different from the first region;

d) an adjuster for adjusting a direction of an optical axis of the second measurement light such that at least part of second surface reflected light enters the polarization optical system, the second surface reflected light being the second measurement light reflected on a surface in the second region; and e) a detector for detecting light having passed through the polarization optical system.

A reflected light detecting method according to the present invention devised in order to solve the aforementioned problem includes the steps of:

a) causing first measurement light in a predetermined polarization direction to enter a first region of a target object having a globally non-planar surface from a first direction;

b) arranging a polarization optical system at a position where at least part of first surface reflected light enters the polarization optical system, the first surface reflected light being the first measurement light reflected on a surface in the first region;

c) causing second measurement light in the same polarization direction as that of the first measurement light to enter a second region from a second direction, the second region being located on the surface of the target object and different from the first region;

d) adjusting a direction of an optical axis of the second measurement light such that at least part of second surface reflected light enters the polarization optical system, the second surface reflected light being the second measurement light reflected on a surface in the second region; and e) detecting light having passed through the polarization optical system.

The first region and the second region are not necessarily flat, but they are preferably flat surfaces with as less roughness as possible, still preferably evenly continuous surfaces. The "evenly continuous surface" refers to a smooth curved surface, such, for example, as a lateral surface of a streamline-shaped vehicle body, in which inclinations of tangential lines of parts in the first region or the second region do not largely differ from one another over the whole region. For example, in a polyhedral target object, it is desirable to set the first region and the second region such that they do not contain edge parts or vertex parts.

The polarization optical system refers to an optical system including an optical member that allows only light in a predetermined polarization direction to pass through, such as a polarizing plate or a polarizing filter.

When light enters a target object, a part of the light is reflected on the surface of the target object, and the rest enters the inside of the target object to be diffusively reflected. In this stage, when the light entering the target object has a predetermined polarization direction, its reflection on the surface of the target object maintains that polarization state, while for the internally reflected light, that polarization state breaks to produce non-polarized light. In the aforementioned illuminating system and illuminating method, both at least part of the surface reflected light (first surface reflected light) of the first measurement light entering the first region on the surface of the target object, and at least part of the surface reflected light (second surface reflected light) of the second measurement light entering the second region enter the common polarization optical system. Moreover, after entering the inside of the target object and being internally reflected, since light resulting from the first measurement light that enters the first region (hereinafter, referred to as "first internally reflected light"), and light resulting from the second measurement light that enters the second region (hereinafter, referred to as "second internally reflected light") are radiated in various directions, parts of these also enter the polarization optical system similarly to the first surface reflected light and the second surface reflected light. In this stage, since the polarization directions of the first measurement light and the second measurement light are the same, the polarization directions of the first surface reflected light and the second surface reflected light are also the same. Accordingly, by configuring the polarization optical system to include an optical member with the same polarization axis as the polarization directions of the first surface reflected light and the second surface reflected light, or an optical member with the polarization axis orthogonal to the polarization directions of the first surface reflected light and the second surface reflected light, or an optical member with a polarization axis intermediate between both, the amounts of the first surface reflected light, the second surface reflected light, the first internally reflected light and the second internally reflected light that pass through the polarization optical system to travel toward the detector can be collectively adjusted.

The polarization optical system may include, as well as a polarizing filter, one or more reflection mirrors for changing the travelling direction of the first surface reflected light or the second surface reflected light such that a large amount of the first surface reflected light and the second surface reflected light travels toward the aforementioned optical member, a collimator lens for focusing the first surface reflected light or the second surface reflected light onto the vicinity of the polarizing filter, and the like.

In the aforementioned reflected light detecting device and reflected light detecting method, each of the first illuminating device and the second illuminating device may be movable relative to the target object. With such a configuration, the first measurement light and the second measurement light can be caused to enter proper spots on the surface of the target object.

Furthermore, in the present invention, the detector preferably includes:

a focusing optical system for focusing the light having passed through the polarization optical system, a parallel optical system for converting the light focused by the focusing optical system into parallel light, an optical path length difference changer for dividing the parallel light into first divided light and second divided light and giving a continuously changing optical path length difference between the first divided light and the second divided light, an imaging optical system for focusing the first divided light and the second divided light to which the continuously changing optical path length difference is given on an imaging plane to form interference light, an interference light detecting unit for detecting an intensity of the interference light, and that has a plurality of pixels arranged on the imaging plane, and a processing unit for obtaining an interferogram of a component contained in the object to be measured based on the intensity of the interference light detected by the interference light detecting unit and acquiring a spectrum through Fourier transform of the interferogram.

In the aforementioned configuration, the light having passed through the polarization optical system is focused on the focusing optical system, and after that, is converted into the parallel light beams by the parallel optical system. Then, after it is divided into the first divided light and the second divided light by the optical path length difference changer, it is focused on the imaging plane by the imaging optical system to form the interference light. In this stage, since the continuously changing optical path length difference is given between the first divided light and the second divided light by the optical path length difference changer, the intensity of the interference light formed on the imaging plane changes in accordance with the change in this optical path length difference. Accordingly, by detecting the intensity of the interference light, the relation between the optical path length difference and the intensity of the interference light, that is, the interferogram is obtained. Hence, through Fourier transform of this interferogram, the spectrum (spectral characteristics) of the light having passed through the polarization optical system can be acquired. Accordingly, by employing, as the polarization optical system, a polarizing plate with the same polarization axis as those of the first surface reflected light and the second surface reflected light, the spectral characteristics of the surface of the target object can be acquired, and by employing a polarizing plate with the polarization axis orthogonal to the polarization axes of the first surface reflected light and the second surface reflected light, the spectral characteristics of the internal components of the target object can be acquired.

Moreover, the first illuminating device preferably causes the first measurement light to enter the first region at the Brewster angle. Herein, when the first region is a curved surface, the first measurement light only has to enter any place in the first region at the Brewster angle.

It is known that in surface reflection, a linearly polarized light component (S-polarized light component) that oscillates in the direction orthogonal to the incident plane (plane including the normal line of the surface of the target object and the incident light) and a linearly polarized light component (P-polarized light component) that oscillates in the direction parallel to the incident plane are reflected at different reflectivities. Specifically, the reflectivity of the P-polarized light component is smaller than the reflectivity of the S-polarized light component, and in particular, the P-polarized light component has an incident angle at which its reflectivity is zero, and this incident angle is called a "Brewster angle". Accordingly, in the aforementioned configuration, since the first measurement light enters the first region at the Brewster angle, the first surface reflected light does not contain a component of P-polarized light due to the relation to the incident plane, which can reduce the amount of the first surface reflected light travelling toward the polarization optical system.

Advantageous Effects of Invention

According to the present invention, the oscillation directions (polarization states) of rays of surface reflected light resulting from rays of measurement light caused to enter a plurality of regions of a target object having a globally non-planar surface from a plurality of directions are made uniform, and the rays of surface reflected light are caused to pass through one polarization optical system. Hence, a large amount of the light passing through the polarization optical system can be switched to be the surface reflected light or to be the internally reflected light. Therefore, the reflected light (the surface reflected light or the internally reflected light) on the surface of the target object can be collectively detected by a detector.

DESCRIPTION OF EMBODIMENTS

Hereafter, an embodiment of a reflected light detecting device according to the present invention is described with reference to the drawings.

[Configuration of Reflected Light Detecting Device]

Figure 1:
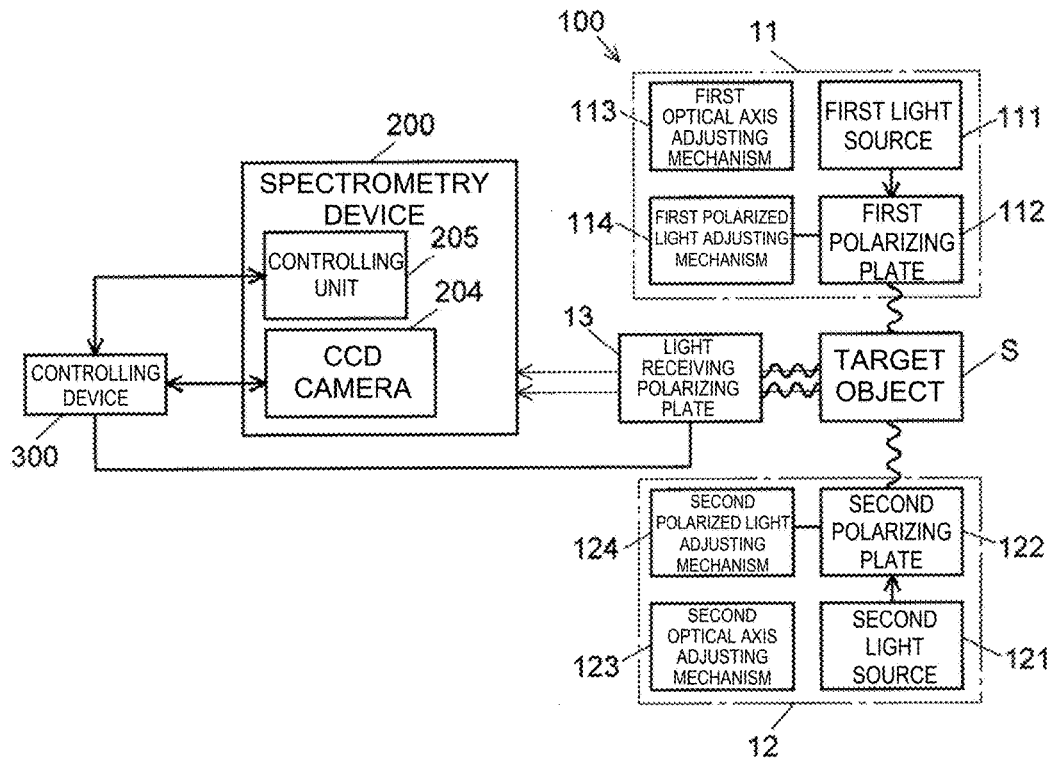
FIG. 1 is a block diagram showing a schematic overall configuration of a reflected light detecting device according to an embodiment of the present invention.
Figure 2:
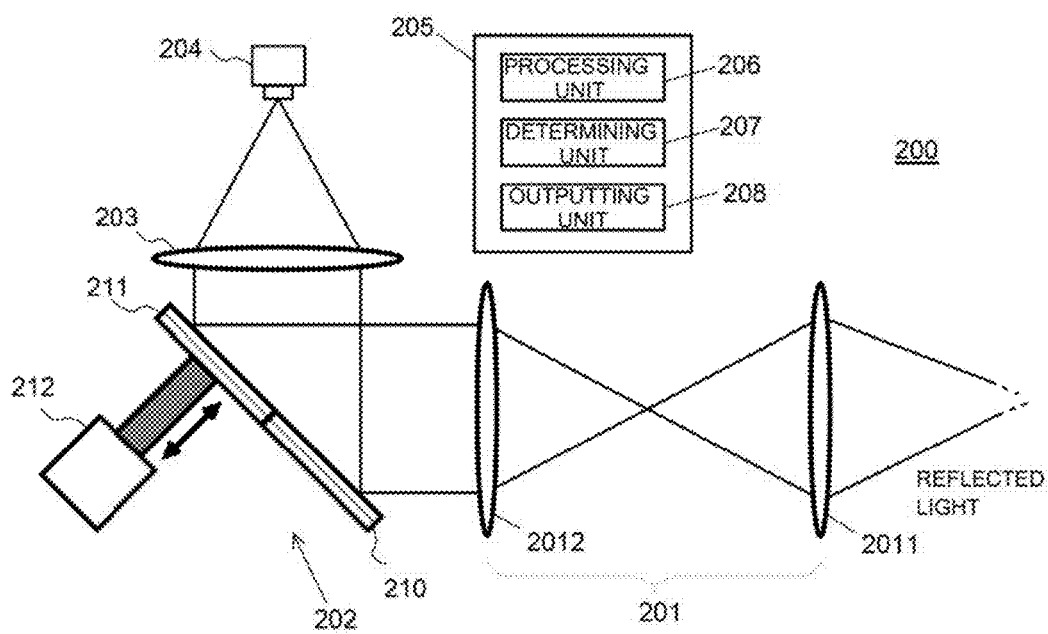
FIG. 2 is a diagram showing a schematic configuration diagram of a spectrometry device.

FIG. 1 is a block diagram of a reflected light detecting device according to the present embodiment. FIG. 2 is a schematic overall configuration diagram of a spectrometry device in the reflected light detecting device. The reflected light detecting device is composed of an illuminating system 100, a spectrometry device 200, and a controlling device 300 for controlling operation of these.

[Configuration of Illuminating System]

The illuminating system 100 includes one first illuminating device 11, one or more second illuminating devices 12, and a light receiving polarizing plate 13. The light receiving polarizing plate 13 corresponds to a polarization optical system of the present invention. As described later in detail, the light receiving polarizing plate 13 is arranged at a position where at least part of reflected light (surface reflected light and internally reflected light) of rays of light that enter a target object S from the first and second illuminating devices 11 and 12 enters the light receiving polarizing plate 13. The spectrometry device 200 is arranged downstream of the light receiving polarizing plate 13.

The positions of the first illuminating device 11 and the second illuminating devices 12 and the number of the second illuminating devices 12 are properly set in accordance with the size and the shape of the target object S. For example, when the target object is a human face, the first illuminating device 11, the second illuminating devices 12 and the light receiving polarizing plate 13 are arranged in front of the target object. Moreover, a plurality of second illuminating devices 12 may be provided, but one second illuminating devices 12 is also sufficient. Meanwhile, when the target object is a horizontally long solid-shaped object such as a body of a vehicle, the first illuminating device 11 is arranged above the target object, and the light receiving polarizing plate 13 is arranged in front of or behind the target object. When the light receiving polarizing plate 13 is arranged in front of the target object, one or more second illuminating devices 12 are arranged on the right side and the left side of the target object or above and below the target object since even if light is cast from behind the target object, its surface reflected light is difficult to be caused to enter the light receiving polarizing plate 13.

The first illuminating device 11 includes: a first light source 111; a first polarizing plate 112 that is arranged between the light source 111 and the target object and that light emitted from the first light source 111 enters; a first optical axis adjusting mechanism 113 for adjusting the optical axis of the light emitted from the first light source 111; and a first polarized light adjusting mechanism 114 for adjusting the polarization direction of the first polarizing plate 112. In this case, the light that is emitted from the first light source 111 and transmitted through the first polarizing plate 112 is first measurement light. Likewise, the second illuminating device 12 includes: a second light source 121; a second polarizing plate 122 that light emitted from the second light source 121 enters; a second optical axis adjusting mechanism 123 for adjusting the optical axis of the light emitted from the second light source 121; and a second polarized light adjusting mechanism 124 for adjusting the polarization direction of the second polarizing plate 122. The light that is emitted from the second light source 121 and transmitted through the second polarizing plate 122 is second measurement light.

Light-emitting diodes (LEDs), by way of example, are used for the first light source 111 and the second light source 121. The wavelength range of the light emitted from the first light source 111 and the second light source 121 is set in accordance with the type of the target object. For example, when the target object is a human face, LEDs including a red wavelength range, which is well transmitted through a skin, are used as the first light source 111 and the second light source 121.

The first light source 111 and the second light source 121 are held on holding units, for example, that can be pivot-driven. Changing the pivot angles of the holding units can change the optical axes of the rays of emitted light, that is, the directions of the optical axes of the first measurement light and second measurement light. The pivot angle may be manually or automatically changed. In the case of the automatic operation, for example, the following configuration is possible.

Optical sensors are arranged near the light receiving polarizing plate 13 and an adjusting mechanism is provided that, based on the detection results of the optical sensors, adjusts the pivot angles of the holding units and adjusts arrangements of the holding units, the target object S and the light receiving polarizing plate 13 such that the intensities of the first measurement light and the second measurement light entering the light receiving polarizing plate 13 become maximum. It is preferable that the pivot angles of the holding units and arrangements of the holding units, the target object S and a light receiver (CCD camera 204 of the spectrometry device 200 mentioned later) are adjusted such that the intensities of the first measurement light and the second measurement light when the rays of light from the installation positions of the first light source 111 and the second light source 121 enter the target object S at Brewster angles are at their maximums, or at their minimums, or to be predetermined setting values. Spots where the rays of light from the first light source 111 and the second light source 121 enter the target object S at the Brewster angles can be specified to some extent when the arrangement of the first light source 111, the second light source 121 and the target object S are determined.

In a structure requiring manual change of the optical axes, the holding unit of the first light source 111 and the holding unit of the second light source 121 serve as the first optical axis adjusting mechanism 113 and the second optical axis adjusting mechanism 123, respectively. In a structure of automatically changing the optical axes, the optical sensor, the holding unit of the first light source 111, and a drive mechanism serve as the first optical axis adjusting mechanism 113, and the optical sensor, the holding unit of the second light source 121, and a drive mechanism serve as the second optical axis adjusting mechanism 123.

[Structure of Spectrometry Device]

As shown in FIG. 2, the spectrometry device 200 includes: an optical system 201 that focuses rays of light that are the first measurement light and the second measurement light reflected on the target object (the surface reflected light and the internally reflected light) and are transmitted through the light receiving polarizing plate 13, and makes them parallel light beams; a phase shifter 202; an imaging lens 203; the CCD camera 204 having a light receiving plane positioned on the imaging plane of the imaging lens 203; and a controlling unit 205 for controlling processing of a detection signal of the CCD camera 204, and drive of the phase shifter 202. The optical system 201 is composed of a condenser lens 2011 and a collimator lens 2012, and these lenses function as a focusing optical system and a parallel optical system according to the present invention, respectively. The phase shifter 202 includes a fixed mirror unit 210, a movable mirror unit 211, and a drive mechanism 212 for moving the movable mirror unit 211 in the direction of the arrow.

The CCD camera 204 includes a two-dimensionally arranged plurality of light receiving elements. The controlling unit 205 includes: a processing unit 206 for obtaining an interferogram from a detection signal by the CCD camera 204 (light receiving elements), and mathematically performing Fourier transform on the interferogram to calculate spectral characteristics (spectrum) that are relative intensities of the light transmitted through the light receiving polarizing plate 13 for respective wavelengths; a determining unit 207 for determining, based on an operation state of the drive mechanism 212, a positional relation between the fixed mirror unit 210 and the movable mirror unit 211 composing the phase shifter 202; and an outputting unit 208 for outputting processing results of the processing unit 206, determination results of the determining unit 207, and the like to outputting devices such as a display and a printer.

[Operation of Reflected Light Detecting Device]

Figure 3A:
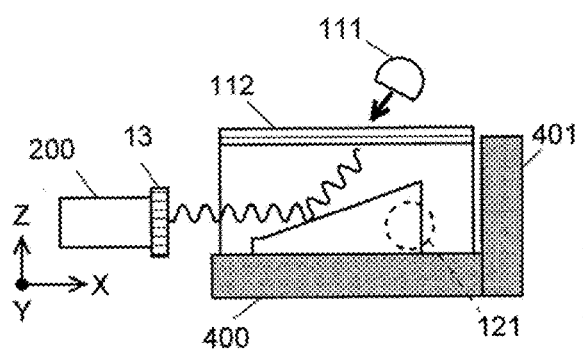
FIG. 3A, FIG. 3B and FIG. 3C are diagrams showing positional relations of a target object, illuminating devices and the spectrometry device.

Next, operation of the reflected light detecting device is described with reference to FIG. 3A, FIG. 3B, FIG. 3C, FIG. 4A and FIG. 4B. Here, for simplifying the explanation, it is assumed that the target object S is a tapered solid shape in bilateral symmetry having substantially flat upper face and right and left lateral faces, and that one first illuminating device 11 and two second illuminating devices 12 are arranged so as to enclose the target object S placed on a rectangular plate-shaped table 400 (see FIG. 3A, FIG. 3B and FIG. 3C). Moreover, in the following description, it is assumed that the upper face of the table 400 is a horizontal plane, and it is regarded that an axis parallel to two opposite sides out of the four sides of the upper face of the table 400 is an X-axis, an axis parallel to the remaining two opposite sides is a Y-axis, and the axis (vertical axis) orthogonal to the X-axis and the Y-axis is a Z-axis. Furthermore, the left side on the sheet of FIG. 3A is regarded as the front, and the right side thereon is regarded as the rear.

The first illuminating device 11 is arranged above the target object S. The second illuminating devices 12 are arranged on the right and left sides of the target object S, respectively. The first polarizing plate 112 of the first illuminating device 11 is arranged parallel to the XY-plane, and the first light source 111 is arranged above the first polarizing plate 112. One polarizing plate 122 of the two second illuminating devices 12 stands on the left side of the table 400 so as to be parallel to the XZ-plane, and the other polarizing plate 122 stands on the right side of the table 400 so as to be parallel to the XZ-plane. Both the second light sources 121 are arranged outside the right and left second polarizing plates 122. The light receiving polarizing plate 13 and the spectrometry device 200 are arranged in front of the target object S.

A light shielding plate 401 is arranged behind the target object S. That is, the target object S is placed in a rectangular box-shaped space having an opening at front side and being formed of the table 400, the first polarizing plate 112, the second polarizing plates 122 and the light shielding plate 401. This allows the reflected light of the first measurement light and the second measurement light entering the target object S to advance toward the light receiving polarizing plate 13 only through the opening of the space.

With the aforementioned configuration, first, the polarization direction (polarization axis) of the first polarizing plate 112 is set to be the X-axis direction, and the polarization direction of the second polarizing plate 122 is set to be the Z-axis direction. Moreover, a polarizing plate with the polarization direction being the Y-axis direction is employed as the light receiving polarizing plate 13. Thereby, all of the positional relations between the first polarizing plate 112 and the second polarizing plate 122, between the first polarizing plate 112 and the light receiving polarizing plate 13, and between the second polarizing plate 122 and the light receiving polarizing plate 13 become crossed nicol where the polarization directions are orthogonal to each other.

Next, the orientation of the optical axis of the light emitted from the first light source 111 and the orientation of the optical axis of the light emitted from the second light source 121 are adjusted by the optical axis adjusting mechanisms 113 and 123 to cause both the first measurement light and the second measurement light to enter the light receiving polarizing plate 13. Here, the optical axis of the light emitted from the first light source 111 is set to be parallel to the XZ-plane, and the optical axis of the light emitted from the second light sources 121 is set to be parallel to the XY-plane.

Subsequently, by emitting the light from the first light source 111, a component, of the light, that oscillates in the direction parallel to the XZ-plane is transmitted through the first polarizing plate 112, and enters a predetermined region (a first region) on the upper face of the target object S as the first measurement light. Then, the component is reflected on the first region to advance toward the light receiving polarizing plate 13. Since an incident plane of the first measurement light (a plane including the optical axis of the first measurement light and the normal line in the first region) is parallel to the XZ-plane, the first measurement light is P-polarized light, and the surface reflected light of the first measurement light (first surface reflected light) is also P-polarized light.

Meanwhile, by emitting the rays of light from the second light sources 121, components, of the rays of light, that oscillate in the direction parallel to the YZ-plane are transmitted through the second polarizing plates 122, and enter predetermined regions (second regions) on the left lateral face and the right lateral face of the target object S as the rays of second measurement light. Then, the components are reflected on the second regions to advance toward the light receiving polarizing plate 13. Since incident planes of the rays of second measurement light (planes including the optical axes of the rays of second measurement light and the normal lines in the second regions) are orthogonal to the YZ-plane, the second measurement light is S-polarized light regarding the relation with the incident plane, while a oscillation direction of the components of the rays of second measurement light toward the light receiving polarizing plate 13 after surface reflection in the second region is the same as that of the first surface reflected light. Accordingly, the first surface reflected light and the second surface reflected light attenuate in passing through the light receiving polarizing plate 13, only internally reflected light from the first measurement light and the internally reflected light from the second measurement light enter the spectrometry device 200.

Figure 3B:
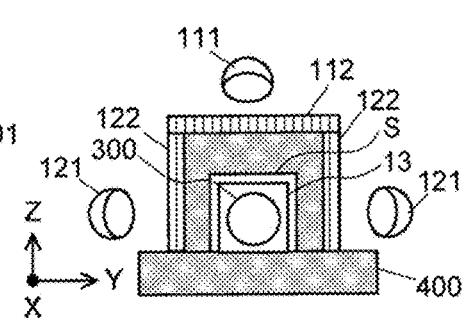
Figure 3C:
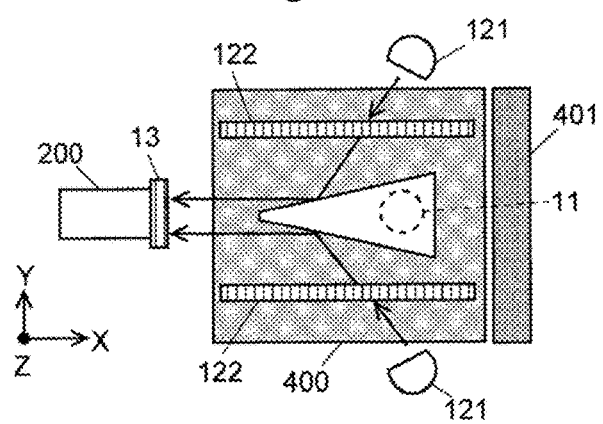
Figure 4A:
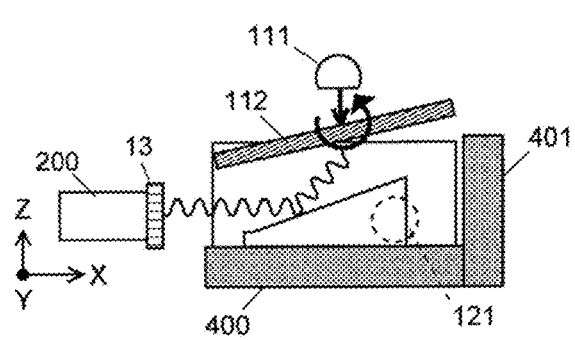
FIG. 4A and FIG. 4B are diagrams showing an example (FIG. 4A) in which the inclination of a polarizing plate of a first illuminating device is changed, and an example (FIG. 4B) in which the inclinations of polarizing plates of first and second illuminating devices.
Figure 4B:
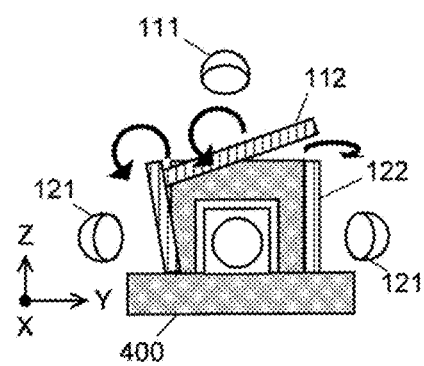

While in the example shown in FIG. 3A to FIG. 3C, the first polarizing plate 112, the second polarizing plate 122 and the light receiving polarizing plate 13 are arranged orthogonal to one another, as shown in FIG. 4A and FIG. 4B, they are not needed to be orthogonal to one another. As long as the polarization directions of the first and second polarizing plates 112 and 122 do not change, they can be properly inclined. For example, FIG. 4A shows an example in which the first polarizing plate 112 is rotated around the Y-axis from the state shown in FIG. 3A to FIG. 3C, and FIG. 4B shows an example in which the first polarizing plate 112 and the left second polarizing plate 122 are rotated around the X-axis and the right second polarizing plate 122 is rotated around the Z-axis from the state shown in FIG. 3A to FIG. 3C. In other words, the polarization direction does not change even when the first polarizing plate 112 is rotated around the X-axis or the Y-axis, and the polarization direction does not change even when the second polarizing plate 122 is rotated around the X-axis and the Z-axis. That is, they can be freely rotated in these directions. While, when the first polarizing plate 112 is rotated around the Z-axis or when the second polarizing plate 122 is rotated around the Y-axis, the polarization direction changes, and hence, there is no degree of freedom of rotation in these directions.

The operation of the reflected light detecting device is described further in detail with reference to FIG. 5A to FIG. 5F. FIG. 5A to FIG. 5F are diagrams showing relations between the polarization directions of the first polarizing plate and the light receiving polarizing plate. In the figures, the arrows indicate the polarization directions (directions of the polarization axes) of the polarizing plates.

Figure 5A:
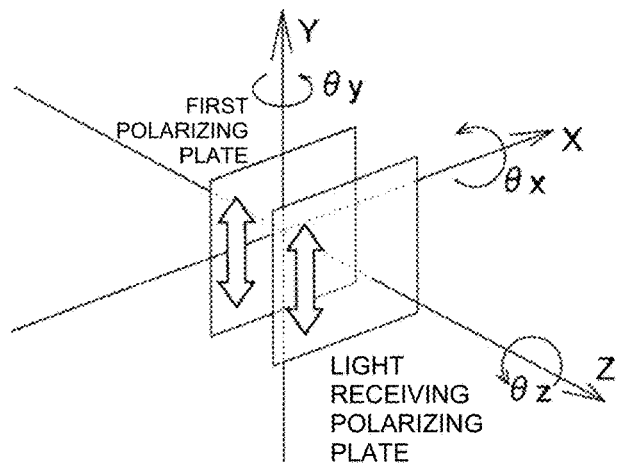
FIG. 5A is a diagram showing a state where the polarization directions of a first polarizing plate and a light receiving polarizing plate are in parallel nicol.
Figure 5B:
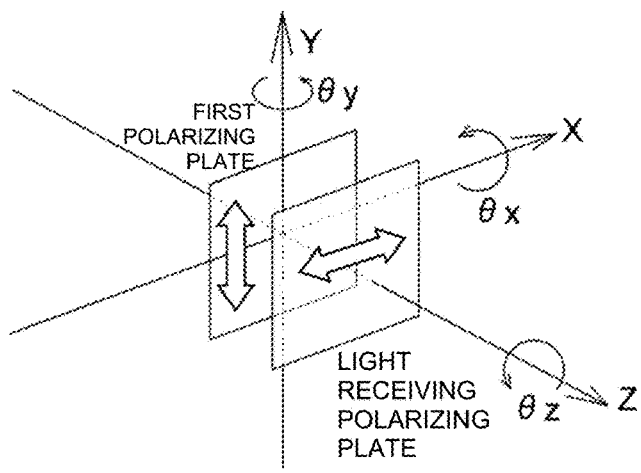
FIG. 5B is a diagram showing a state where the polarization directions of the first polarizing plate and the light receiving polarizing plate are in crossed nicol.
Figure 5C:
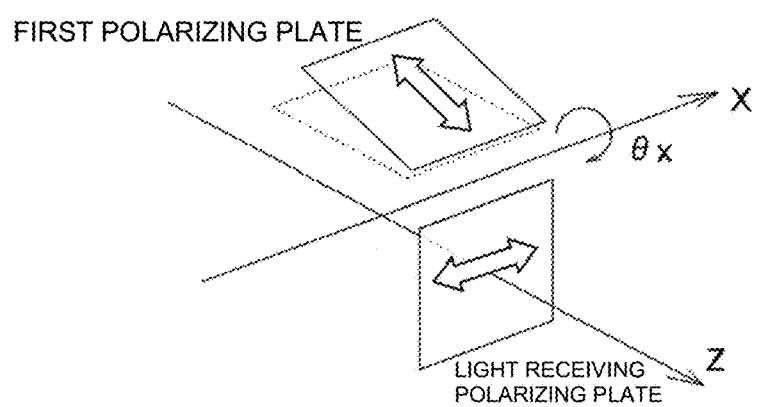
FIG. 5C is a diagram for explaining a relation between the polarization directions of the first polarizing plate and the light receiving polarizing plate after a rotation of the first polarizing plate around the X-axis.
Figure 5D:
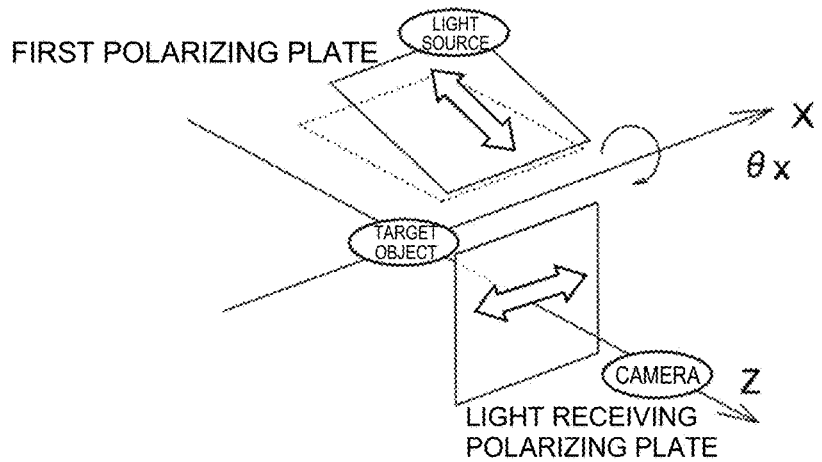
FIG. 5D is a diagram for explaining a positional relation between a light source, a target object and a camera and a relation between the polarization directions of the first polarizing plate and the light receiving polarizing plate after a rotation of the first polarizing plate around the X-axis.
Figure 5E:
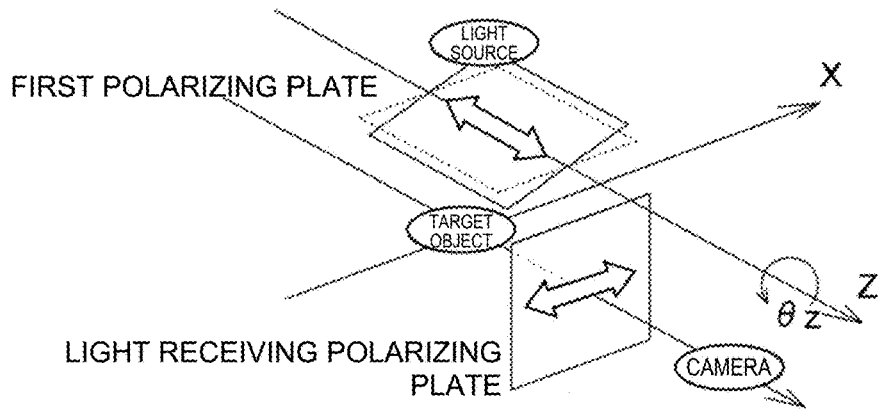
FIG. 5E is a diagram for explaining the positional relation between the light source, the target object and the camera and a relation between the polarization directions of the first polarizing plate and the light receiving polarizing plate after a rotation of the first polarizing plate around the Z-axis.

FIG. 5A and FIG. 5B show a parallel nicol state (a positional relation where the polarization directions are parallel to each other) and a crossed nicol state (a positional relation where the polarization directions are orthogonal to each other), respectively when the first polarizing plate and light receiving polarizing plate are parallelly arranged. Meanwhile, FIG. 5C shows a state where the first polarizing plate is rotated around the X-axis from the state shown in FIG. 5B. In the state shown in FIG. 5C, in the case of emitting light to the target object from the light source above the first polarizing plate and surface-reflecting it toward the light receiving polarizing plate (in the Z-axis direction) as shown in FIG. 5D, the relation between the polarization direction of the first polarizing plate and the polarization direction of the light receiving polarizing plate is constant regardless of the inclination of the first polarizing plate. FIG. 5E shows a state where the first polarizing plate is rotated around the X-axis and then further rotated around the Z-axis from the state shown in FIG. 5B. In the state shown in FIG. 5D, in the case of emitting light to the target object from the light source above the first polarizing plate and surface-reflecting it toward the light receiving polarizing plate (in the Z-axis direction), the relation between the polarization direction of the first polarizing plate and the polarization direction of the light receiving polarizing plate is also constant regardless of the inclination of the first polarizing plate. These apply to any of positional relations in a parallel nicol and a crossed nicol between the first polarizing plate and the light receiving polarizing plate.

Figure 5F:
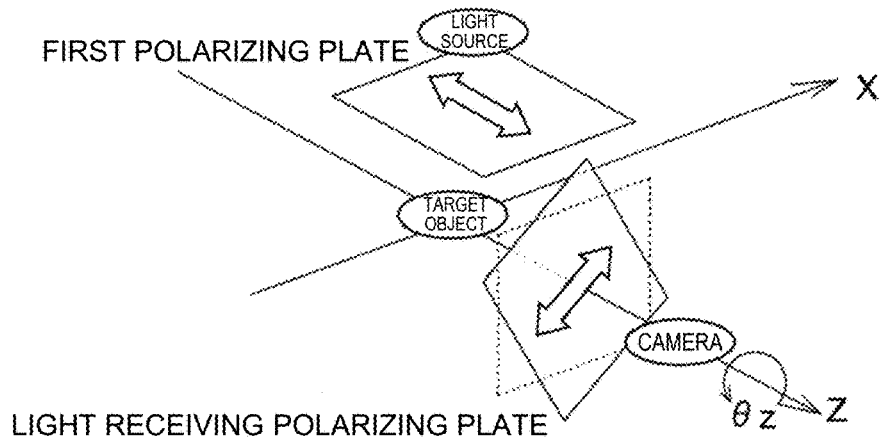
FIG. 5F is a diagram for explaining the positional relation between the light source, the target object and the camera and a relation between the polarization directions of the first polarizing plate and the light receiving polarizing plate after a rotation of the light receiving polarizing plate around the Z-axis.

FIG. 5F shows a state where the first polarizing plate is rotated around the X-axis and the light receiving polarizing plate is rotated around the Z-axis from the state shown in FIG. 5B. In the state shown in FIG. 5D, in the case of emitting light to the target object from the light source above the first polarizing plate and surface-reflecting toward the light receiving polarizing plate (in the Z-axis direction), the relation between the polarization direction of the first polarizing plate and the polarization direction of the light receiving polarizing plate breaks. The same applies to the case of rotating the light receiving polarizing plate around the Y-axis. Moreover, these apply to any of positional relations of a parallel nicol and a crossed nicol between the first polarizing plate and the optical element. However, after the first polarizing plate is rotated around the X-axis from the state shown in FIG. 5B, when the first polarizing plate is further rotated around the Y-axis or the light receiving polarizing plate is rotated around the Z-axis (the state shown FIG. 5F), the amount of the light that is transmitted through the first polarizing plate being transmitted through the light receiving polarizing plate can be adjusted.

[Measurement Results 1]

Next, specific measurement results of spectral characteristics are presented.

Figure 6:
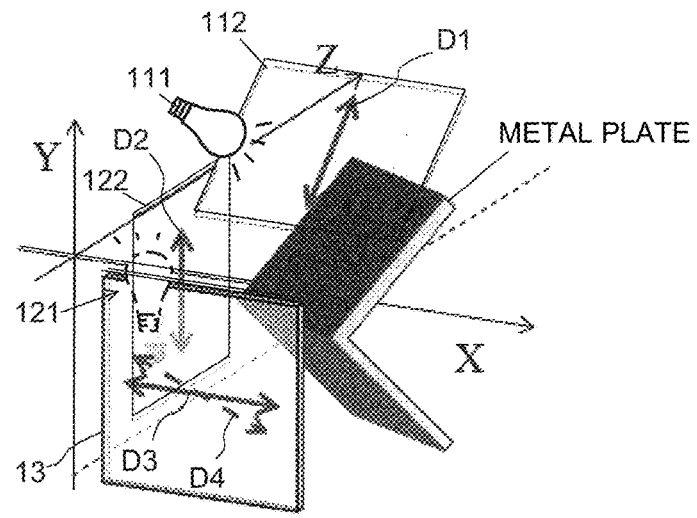
FIG. 6 is a schematic diagram of an experimental system for measuring spectral characteristics in casting light from two white LEDs onto a red paint-applied metal plate.

Spectral characteristics of reflected light arising on a metal plate (a target object S) having an L-shaped cross section and a surface of which red paint is painted were measured where rays of light were cast from two white LEDs (the first light source 111 and the second light source 121 each of which had a wavelength band within 400 to 800 nm) onto two different faces (a face A and a face B) of the metal plate. FIG. 6 shows an arrangement of the two white LEDs, the first and second polarizing plates 112 and 122, the metal plate, and the light receiving polarizing plate 13. Moreover, the aforementioned spectrometry device 200 not shown in FIG. 6 is arranged at a position where light having passed through the light receiving polarizing plate 13 enters.

As shown in FIG. 6, rays of light emitted from the two white LEDs are cast onto the orthogonal two faces (the face A and the face B) of the metal plate, respectively. Between the white LEDs and the metal plate, the polarizing plates (the first polarizing plate 112 and the second polarizing plate 122) are arranged. The light emitted from the upper white LED (first light source 111) enters the face A of the metal plate as polarized light whose polarization axis is in the direction indicated by an arrow D1, and the light emitted from the lower white LED (second light source 121) enters the face B of the metal plate as polarized light whose polarization axis is in the direction indicated by an arrow D2. Moreover, the light receiving polarizing plate 13 is arranged at a position where at least part of rays of light emitted from two white LEDs and surface-reflected on the metal plate enters.

Figure 7A:
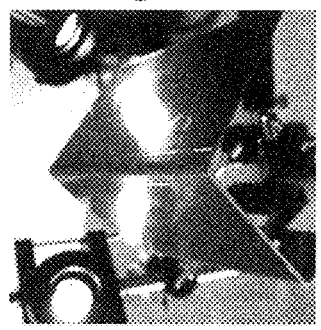
FIG. 7A and FIG. 7B show a visual image (FIG. 7A) and a CCD image (FIG. 7B) of the metal plate in casting the light from the two white LEDs.
Figure 7B:

When the polarization axis of the light receiving polarizing plate 13 is in the direction indicated by an arrow D3 in FIG. 6, that is, when the polarization axis of the light receiving polarizing plate 13 and the polarization axes of the polarizing plates 112 and 122 on the white LED sides are in parallel nicol, a visual image of the metal plate, and a detection image of the metal plate taken by the CCD camera 204 of the spectrometry device 200 (referred to as "CCD image") are as shown in FIG. 7A and FIG. 7B, respectively. It can be seen from these figures that the rays of light emitted from the white LEDs are cast equivalently onto both the face A and the face B.

Figure 8:
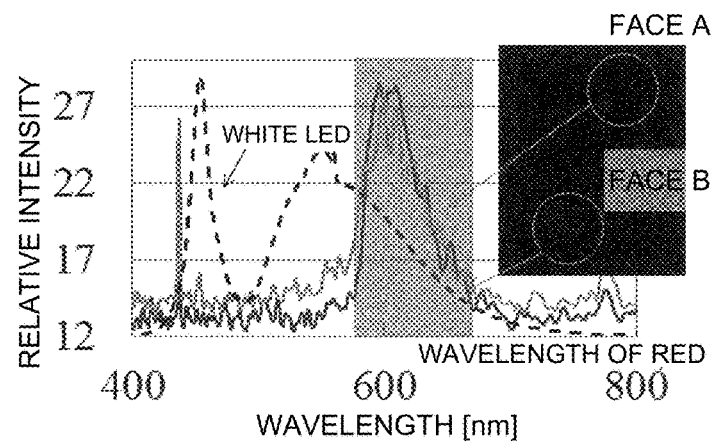
FIG. 8 shows spectral characteristics of reflected light in a crossed nicol relation between the polarization directions of the first polarizing plate and the light receiving polarizing plate.

FIG. 8 shows the measurement results (spectra) by the spectrometry device 200 when the light receiving polarizing plate 13 and the first and second polarizing plates 112 and 122 are in crossed nicol. FIG. 8 shows a spectrum of light (white LED) in the case where rays of light emitted from the white LEDs (the first light source 111 and the second light source 121) directly enters the light receiving polarizing plate 13, a spectrum of light in the case where w light emitted from the white LED (first light source 111) passes through the first polarizing plate 112, reflects on the face A, and enters the light receiving polarizing plate 13, and a spectrum of light in the case where light emitted the white LED (second light source 121) passes through the second polarizing plate 122, reflects on the face B, and enters the light receiving polarizing plate 13.

As shown in FIG. 8, the spectrum of the light emitted from the white LED has peaks near 450 nm of wavelength and near 550 nm of wavelength. On the contrary, both the spectrum of the light from the face A and the spectrum of the light from the face B do not have the peak components of the spectrum of the light emitted from the white LED. The reason is that the polarization directions of the rays of surface reflected light on the face A and the face B are orthogonal to the polarization axis of the light receiving polarizing plate 13, and hence, the rays of surface reflected light on the faces do not pass through the light receiving polarizing plate 13, and only a part of the internally reflected light as non-polarized light passes through the light receiving polarizing plate 13. Accordingly, the spectra of the rays of light from the face A and the face B represent spectra of the rays of internally reflected light on the faces. The peak wavelengths (580 nm to 650 nm) seen in the spectra of the rays of light from the face A and the face B correspond to the wavelength of the color (red) of the paint on the face A and the face B. From this result, it can be seen that by setting the light receiving polarizing plate 13 and the first and second polarizing plates 112 and 122 in a crossed nicol relation in the reflected light detecting device according to the present embodiment, the spectral characteristics of the paint components on the face A and the face B can be obtained.

Figure 9:
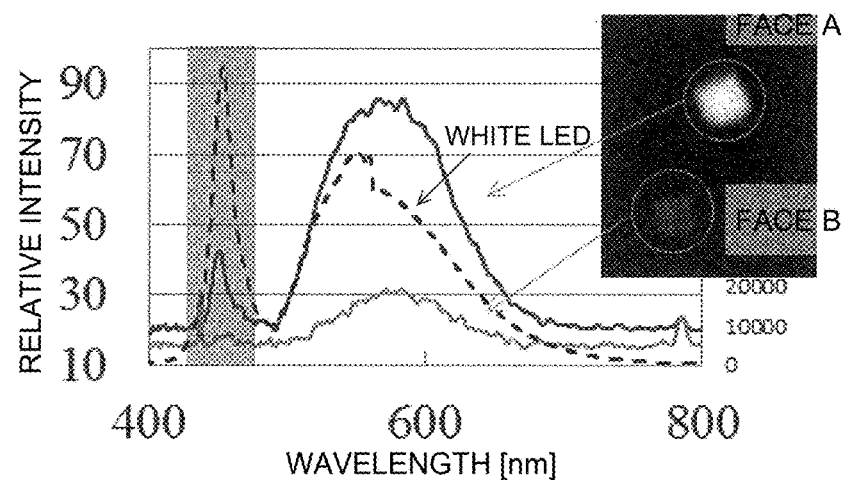
FIG. 9 shows spectral characteristics of reflected light in a displacement between the polarization directions of the first polarizing plate and the light receiving polarizing plate by 15°.

FIG. 9 shows the measurement results (spectra) by the spectrometry device 200 when the polarization axis of the light receiving polarizing plate 13 is in the direction indicated by an arrow D4 in FIG. 6, that is, when the direction of the polarization axis of the light receiving polarizing plate 13 is shifted by 15° from the directions of the polarization axes of the first and second polarizing plates 112 and 122. Similarly to FIG. 8, FIG. 9 shows a spectrum of light (white LED) resulting from the rays of light emitted from the white LEDs directly entering the light receiving polarizing plate 13, a spectrum of light reflected on the face A, and entering the light receiving polarizing plate 13, and a spectrum of light reflected on the face B, and entering the light receiving polarizing plate 13.

As is different from FIG. 8, the spectrum of the light from the face A and the spectrum of the light from the face B shown in FIG. 9 have peak components similar to the two peaks in the spectrum of the light emitted from the white LED. The reason is that the polarization directions of the rays of surface reflected light on the face A and the face B are shifted by 15° from the state where they are orthogonal to the polarization axis of the light receiving polarizing plate 13, and a part of the rays of surface reflected light on the faces also passes through the light receiving polarizing plate 13 along with a part of the non-polarized internally reflected light. Accordingly, the spectra of the rays of light from the face A and the face B represent spectra of the rays of light containing the surface reflected light and the internally reflected light on the faces.

Also when the light receiving polarizing plate 13 and the first and second polarizing plates 112 and 122 are in a parallel nicol relation, both the surface reflected light and the internally reflected light from the face A and the face B pass through the light receiving polarizing plate 13. In this case, the light amount of the surface reflected light is predominantly more than the light amount of the internally reflected light, and the intensity of the internally reflected light is hidden due to the intensity of the surface reflected light. Hence, it is difficult to obtain the spectral characteristics of the internally reflected light. For dealing with this, by properly adjusting the angles of the polarization axes of the light receiving polarizing plate 13 and the first and second polarizing plates 112 and 122, the spectral characteristics of both the surface reflected light and the internally reflected light on the face A and the face B can be simultaneously obtained.

In FIG. 9, the peak intensities in the spectrum of the light from the face A are larger than the peak intensities in the spectrum of the light from the face B. This is because the surface reflected light from the face A more passes through the light receiving polarizing plate 13 than the surface reflected light from the face B.

According to the above, it can be seen that by adjusting the relations between the polarization axes of the first and second polarizing plates 112 and 122 and the polarization axis of the light receiving polarizing plate 13, the light amounts of the surface reflected light and the internally reflected light entering the spectrometry device 200 can be adjusted.

[Measurement Results 2]

Figure 10:
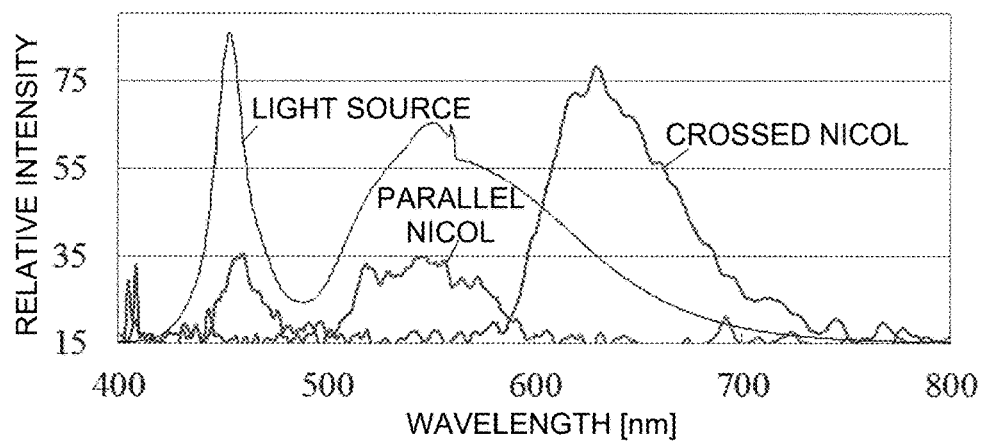
FIG. 10 shows spectral characteristics in casting light from the two white LEDs onto a red paint-applied miniature car.
Figure 11A:
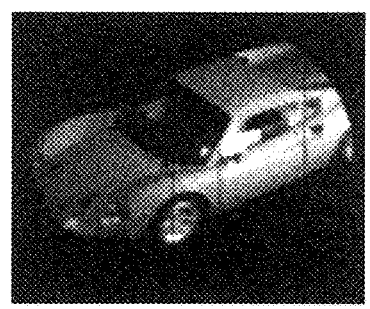
FIG. 11A and FIG. 11B show a CCD image (FIG. 11A) in a crossed nicol relation between the polarization directions of the first polarizing plate and the light receiving polarizing plate, and a CCD image (FIG. 11B) in a parallel nicol relation between those.
Figure 11B:
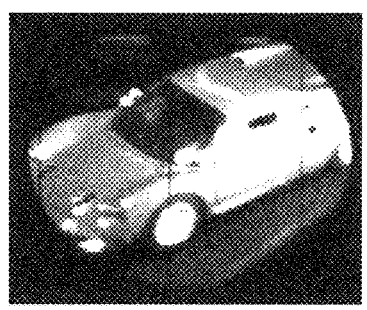

Next, instead of the metal plate, spectral characteristics of reflected light in casting the rays of light from the two white LEDs onto a vehicle body of a miniature car to the surface of which red paint was painted were measured. The configuration of the device used is the same as for the measurement results 1. FIG. 10 shows the results. FIG. 10 shows spectral characteristics when the light receiving polarizing plate 13 and the first and second polarizing plates 112 and 122 are in a crossed nicol relation and in a parallel nicol relation, and spectral characteristics of the light source. FIG. 11A and FIG. 11B show CCD images in a crossed nicol relation and in a parallel nicol relation.

It can be seen also from FIG. 10, FIG. 11A and FIG. 11B that the reflected light detecting device according to the present embodiment can detect the spectral characteristics of the internally reflected light when the light receiving polarizing plate 13 and the first and second polarizing plates 112 and 122 are in a crossed nicol relation, and the spectral characteristics of the surface reflected light when they are in a parallel nicol relation.

REFERENCE SIGNS LIST

11 . . . First Illuminating Device
111 . . . First Light Source
112 . . . First Polarizing Plate
113 . . . Optical Axis Adjusting Mechanism
114 . . . Polarized Light Adjusting Mechanism
12 . . . Second Illuminating Device
121 . . . Second Light Source
122 . . . Second Polarizing Plate
123 . . . Optical Axis Adjusting Mechanism
124 . . . Polarized Light Adjusting Mechanism
13 . . . Light Receiving Polarizing Plate
100 . . . Illuminating System
200 . . . Spectrometry Device
201 . . . Optical System
2011 . . . Condenser Lens
2012 . . . Collimator Lens
202 . . . Phase Shifter
204 . . . CCD Camera
300 . . . Controlling Device

The invention claimed is:

1. A reflected light detecting device comprising:
a) a first illuminating device configured to cause first measurement light in a predetermined polarization direction to enter a first region of a target object having a globally non-planar surface;
b) a polarization optical system arranged at a position where at least part of first surface reflected light enters the polarization optical system, the first surface reflected light being the first measurement light reflected on a surface in the first region;
c) a second illuminating device configured to cause second measurement light to enter a second region, such that a polarization direction of second surface reflected light is the same as that of the first surface reflected light, the second region being located on the surface of the target object and different from the first region, the second surface reflected light being the second measurement light reflected on a surface in the second region;
d) an adjuster configured to adjust a direction of an optical axis of the second measurement light such that at least part of the second surface reflected light enters the polarization optical system; and
e) a detector configured to detect light having passed through the polarization optical system, wherein the detector includes:
a focusing optical system for focusing the light having passed through the polarization optical system, a parallel optical system for converting the light focused by the focusing optical system into parallel light, an optical path length difference changer configured to divide the parallel light into first divided light and second divided light and configured to give a continuously changing optical path length difference between the first divided light and the second divided light, an imaging optical system configured to focus the first divided light and the second divided light to which the continuously changing optical path length difference is given on an imaging plane to form interference light, an interference light detecting unit configured to detect an intensity of the interference light, and that has a plurality of pixels arranged on the imaging plane, and a processing unit configured to obtain an interferogram of a component contained in the target object based on the intensity of the interference light detected by the interference light detecting unit and configured to acquire a spectrum through Fourier transform of the interferogram.

2. The reflected light detecting device according to claim 1, wherein each of the first illuminating device and the second illuminating device is movable relative to the target object.

3. The reflected light detecting device according to claim 1, wherein the first illuminating device causes the first measurement light to enter the first region at a Brewster angle.

4. The reflected light detecting device according to claim 1, further comprising a first optical axis adjuster configured to adjust an optical axis of the first measurement light.

5. The reflected light detecting device according to claim 1, wherein
the second region is composed of a plurality of different regions on the surface of the target object, and
the second illuminating device includes a plurality of light sources for casting rays of second measurement light onto each of the plurality of second regions.

6. A reflected light detecting method comprising the steps of:

a) causing first measurement light in a predetermined polarization direction to enter a first region of a target object having a globally non-planar surface;

b) arranging a polarization optical system at a position where at least part of first surface reflected light enters the polarization optical system, the first surface reflected light being the first measurement light reflected on a surface in the first region;

c) causing second measurement light to enter a second region, such that a polarization direction of second surface reflected light is the same as that of the first surface reflected light, the second region being located on the surface of the target object and different from the first region, the second surface reflected light being the second measurement light reflected on a surface in the second region;

d) adjusting a direction of an optical axis of the second measurement light such that at least part of the second surface reflected light enters the polarization optical system;

e) focusing light having passed through the polarization optical system by a focusing optical system;

f) converting the light focused by the focusing optical system into parallel light by a parallel optical system;

g) dividing the parallel light into first divided light and second divided light and giving a continuously changing optical path length difference between the first divided light and the second divided light by an optical path length difference changer;

h) focusing, on an imaging plane, the first divided light and the second divided light to which the continuously changing optical path length difference is given to form interference light by an imaging optical system;

i) detecting an intensity of the interference light by an interference light detecting unit that has a plurality of pixels arranged on the imaging plane; and j) obtaining an interferogram of a component contained in the target object based on the intensity of the interference light detected by the interference light detecting unit and acquiring a spectrum through Fourier transform of the interferogram by a processing unit.

* * * * *